United States Patent [19]
Burton et al.

[11] Patent Number: 5,588,965
[45] Date of Patent: Dec. 31, 1996

[54] DEVICE FOR SLOWLY DILATING THE PROSTATIC URETHRA

[75] Inventors: John H. Burton; Bradford G. Staehle, both of Minnetonka, Minn.

[73] Assignee: American Medical Systems, Inc., Minnetonka, Minn.

[21] Appl. No.: 399,789

[22] Filed: Mar. 7, 1995

[51] Int. Cl.⁶ .................................................. A61M 29/00
[52] U.S. Cl. ............................................. 604/101; 606/192
[58] Field of Search .................................. 604/96, 101, 49, 604/54; 606/192, 194

[56] References Cited

U.S. PATENT DOCUMENTS

| | | | |
|---|---|---|---|
| 2,799,273 | 7/1957 | Oddo . | |
| 4,434,797 | 3/1984 | Silander | 128/343 |
| 4,480,642 | 11/1984 | Stoy et al. | 128/341 |
| 4,610,662 | 9/1986 | Weikl et al. | 604/53 |
| 4,636,195 | 1/1987 | Wolinsky | 604/53 |
| 4,655,771 | 4/1987 | Wallsten | 128/334 R |
| 4,660,560 | 4/1987 | Klein | 128/344 |
| 4,718,410 | 1/1988 | Hakky | 128/79 |
| 4,732,152 | 3/1988 | Wallsten et al. | 128/343 |
| 4,762,128 | 8/1988 | Rosenbluth | 604/96 |
| 4,886,062 | 12/1989 | Wiktor | 128/343 |
| 4,932,938 | 6/1990 | Goldberg et al. | 604/96 |
| 4,932,956 | 6/1990 | Reddy et al. | 606/192 |
| 4,932,958 | 6/1990 | Reddy et al. | 604/96 |
| 4,950,227 | 8/1990 | Savin et al. | 604/8 |
| 4,955,859 | 9/1990 | Zilber | 604/8 |
| 4,973,301 | 11/1990 | Nissenkorn | 604/8 |
| 4,994,047 | 2/1991 | Walker et al. . | |
| 5,002,558 | 3/1991 | Klein et al. | 606/192 |
| 5,007,898 | 4/1991 | Rosenbluth et al. | 604/54 |
| 5,071,429 | 12/1991 | Pinchuk et al. | 606/192 |
| 5,084,016 | 1/1992 | Freeman et al. . | |
| 5,084,060 | 1/1992 | Freund et al. | 606/192 |
| 5,085,664 | 2/1992 | Bozzo | 606/191 |
| 5,098,374 | 3/1992 | Othel-Jacobsen et al. | 604/8 |
| 5,104,377 | 4/1992 | Levine | 604/101 |
| 5,152,776 | 10/1992 | Pinchuk . | |
| 5,163,952 | 11/1992 | Froix | 623/1 |
| 5,167,614 | 12/1992 | Tessmann et al. | 604/8 |
| 5,167,627 | 12/1992 | Clegg et al. . | |
| 5,178,148 | 1/1993 | Lacoste et al. | 128/660.03 |
| 5,188,596 | 2/1993 | Condon et al. | 604/101 |
| 5,192,289 | 3/1993 | Jessen | 606/155 |
| 5,209,725 | 5/1993 | Roth | 604/53 |
| 5,224,953 | 7/1993 | Morgentaler | 606/192 |
| 5,258,020 | 11/1993 | Froix | 623/1 |
| 5,269,802 | 12/1993 | Garber | 606/191 |
| 5,282,860 | 2/1994 | Matsuno et al. | 623/12 |
| 5,419,763 | 5/1995 | Hildebrand | 604/54 |
| 5,499,994 | 3/1996 | Tihon et al. | 606/192 |
| 5,527,336 | 6/1996 | Rosenbluth et al. | 606/192 |

FOREIGN PATENT DOCUMENTS

| | | |
|---|---|---|
| 576602 | 3/1993 | Japan . |
| 576603 | 3/1993 | Japan . |
| 2035350 | 6/1980 | United Kingdom . |
| 2139898 | 11/1984 | United Kingdom . |

Primary Examiner—Corrine M. McDermott
Attorney, Agent, or Firm—Peter C. Richardson; Lawrence C. Akers; J. Trevor Lumb

[57] ABSTRACT

A device for dilating at least an obstructed portion of the urethra, includes a urinary catheter having a proximal portion and a distal portion; a dilation balloon capable of expanding radially outwardly disposed between the proximal and distal portion of the catheter; and a pressure source capable of sequentially contracting under pressure. The pressure source and dilation balloon are in fluid communication through a conduit which enables fluid to flow from the pressure source to the dilation balloon at a predetermined gradual rate when the pressure source is contracting, whereby the balloon expands gradually radially outwardly to effect the slow dilation of the urethra. A method for dilating the obstructed portion of the urethra and for treating prostatic hyperplasia is also provided.

20 Claims, 4 Drawing Sheets

DEVICE FOR SLOWLY DILATING THE PROSTATIC URETHRA

BACKGROUND OF THE INVENTION

This invention relates generally to dilation devices for the urethra and to the treatment of hypertrophy of the prostate gland. More specifically it relates to novel devices for slowly dilating obstructed potions of the urethra, and to concomitant methods for slowly dilating an obstructed potion of the urethra and for treating benign prostate hyperplasia (BPH).

Benign prostate hyperplasia is a condition which affects well over 50% of the male population over 50 years of age. The treatment of BPH is a matter of great medical and commercial impotence. On a worldwide basis, upwards of four billion dollars are spent annually in the treatment of this condition.

There are many devices, techniques and methods which are presently being employed for treating BPH. Surgical treatment of hypertrophy of the prostate has been a routine procedure for many years. One method of such surgical treatment is open prostatectomy wherein the gland is totally or partially removed. Another method of surgical treatment is transurethral resection of the prostate (TURP). However while surgical treatment can be effective it remains an extremely invasive procedure which is debilitating, painful and often traumatic to the patient. Various complications including impotence, incontinence, bleeding, infection and other undesirable problems attendant with such surge can result. The need for less invasive procedures is therefore of considerable importance.

Among the less invasive procedures now being employed is that of using catheters which are placed in the external opening of the urethra and into at least the obstructed potions of the urethra which allow the passage of urine from the bladder by way of the catheter lumen. These urinary catheters typically employ a positioning or retention balloon at the distal tip which, at the bladder neck, when inflated, prevents the expulsion of the catheter from the body. Illustrative of such positioning balloon catheters are those known in the a as Foley catheters.

It has also been proposed to utilize inflation balloons in addition to positioning balloons for the purpose of dilating obstructed portions of the urethra. Illustrative of such type balloons are those described in U.S. Pat. No. 4,932,958 to Reddy.

It has also been proposed to utilize heat in combination with such catheters for treating the enlarged portion of the prostate, such heat being provided by a variety of means including the use of microwave or laser energy.

Again, while these methods and devices are useful, the search for even less invasive devices and procedures continues. The need for devices and procedures which will result in less pain and discomfort to the patient is of substantial interest, as is the desirability of providing means and devices which will provide for longer term patency of a dilated urethra, i.e. to effect a longer lasting result on relieving the obstruction in the urethra caused by the hypertrophied prostate gland. The latter, due to its resilient fibrous structure and large bulk tends to rebound after treatment of the obstructed urethra is completed, resulting in renewed obstruction.

It would be very desirable, therefore, to provide devices and methods for treating BPH which would be much less invasive and painful, and which would result in dilated urethras of longer patency.

Illustrative of a somewhat less invasive approach is found in the U.S. Pat. No. 4,762,128 to Rosenbluth. This patent discloses an expansion catheter having a rapidly expandable tubular stent associated therewith, which is adapted for transurethral insertion via the external opening of the urethra and for placement within an obstructed region of the urethral lumen caused by a hypertrophied prostate gland. Removal of the expansion catheter leaving in place an expanded tubular stent may result in long term patency of the urethral lumen. Though the stent is also adapted to be removable from the urethra, the intent of the device is to establish a long-term implant.

In U.S. Pat. 5,163,952 to Froix there is disclosed an expandable stent for use in a lumen defined by a wall of a vessel, which illustratively is defined as an arterial vessel in the heart. The polymeric stent has a built-in elastic predetermined diameter and a memory of a diameter greater than the predetermined diameter which is assumed upon activation of a thermal activation point by the adsorption of heat by the plastic, adsorption of liquid by the plastic, or a change in the pH of the liquid surrounding the plastic.

In U.S. Pat. No. 5,084,060 there is provided an apparatus for applying fluidic pressure to the inside of a body vessel during selected intervals to incrementally enlarge the lumen of the vessel.

In U.S. Pat. No. 4,660,560 to Klein there is disclosed a method for treating obstructive prostatism which comprises measuring the distance between the bladder neck and the veru montanum, inserting a dilating catheter into the urethra, and positioning the same, such as through the use of a positioning balloon which can be located in the bladder neck.

Commonly-assigned U.S. Pat. No. 5,499,994, issued Mar. 19, 1996, discloses a method and device for slowly dilating the urethra utilizing a hollow member permitting urination therethrough from the bladder, and hydrophilic means associated therewith which are capable of absorbing water and slowly swelling, thereby dilating the urethra.

SUMMARY OF THE INVENTION

In its broadest context, the present invention relates to a device for slowly dilating an obstructed portion of the urethra, which comprises a urinary catheter, for insertion in the prostatic urethra, having a proximal portion and a distal portion. Disposed on the catheter between the proximal and distal portion is dilation means having a length of at least that of the obstructed portion of the urethra. Also provided is pressure responsive means which is capable of sequentially contracting under pressure, the pressure responsive means and the dilation means being in fluid communication with each other. When the pressure responsive means contracts under pressure, fluid flows therefrom into the dilation means at a predetermined rate to cause the dilation means to expand gradually (and controllably) in a radially outwardly direction, and with sufficient impacting force to cause the obstructed portion of the urethra to dilate to a desired diameter and configuration.

Also in its broadest context, the present invention provides a method for slowly dilating an obstructed portion of a urethra by the sequential transfer of fluid from pressure responsive means, which is capable of expanding and contracting, into dilation means which are thereby radially expanded, the expanded dilation means thereby impacting upon the obstructed portion of the urethra with sufficient, and preferably constant, force to cause the latter to gradually dilate to a desired diameter and configuration.

The present invention also provides a method for treating benign prostatic hyperplasia which comprises the aforesaid method of dilating an obstructed portion of the urethra thereby relieving the obstruction caused by the hypertrophy of the prostate gland.

In one embodiment of this invention, a single inflation/deflation lumen is provided to effect initially the full inflation of the pressure responsive means, and (less than complete) inflation of the dilation means. In the latter case, the extent of dilation is thereby not adequate, or only partially adequate, to dilate the urethra in the manner desired. In this embodiment the subsequent contraction (and at least partial deflation) of the pressure responsive means results in the necessary full inflation of the dilation means thereby resulting in the dilation of the urethra.

In a preferred embodiment of this invention, the pressure responsive means is disposed at or near the distal portion of the catheter and is capable of initially being inflated to a maximum extent due to the onset of fluid, from a single inflation lumen or conduit. This lumen can also act to transfer fluid to the dilation means upon contraction of the pressure responsive means. However, it is also preferred that the flow of liquid from the pressure responsive means, when it is in a contracting mode, be effected through a separately disposed conduit or lumen, as hereinafter described. In this embodiment, the flow of fluid proceeds at a controlled rate, typically through fluid resistor means, which can be of the kind known in the art.

The slow or gradual dilation of the urethra has the significant advantage of alleviating or lessening the discomfort felt by the patient which is the concomitant effect when rapid dilation of the urethra occurs, i.e. on the order of 10 minutes or less, as is the case with the usual dilation currently effected by most prior art devices. In the context of this invention, an expansion rate of between about 5 French and about 20 French over a 24 hour period is desirable to effect the dilation of at least the obstructed portion of the urethra to a maximum or desired diameter and configuration.

In accordance with this invention, the dilation means, disposed on the catheter is usually in the form of a dilation balloon having an outer surface capable of expanding radially outwardly for a period of at least about 30 minutes. The length of the dilation balloon on the catheter should correspond to the length of at least that of the obstructed portion of the urethra. The inflation balloon can be elastic without a defined limit of intrinsic expansion or can also have a defined shape and an intrinsic limit to expansion.

The pressure responsive means can optionally be in the form of an expandable and contractible balloon which can also act as a positioning balloon when located in the area of the bladder neck of the body. However, a separate positioning balloon can also be disposed as part of the device of this invention as, for example, in the area of the bulbous urethra. However, other suitable means can be employed to fix or position the device of this invention.

Another aspect of this invention is the fact that it can be adapted to remain in the urethra for extended periods of time before removal. Such an extended presence can be on the order of at least about 5 days to about 30 days, the latter being a desirable upper limit because of clinical efficacy and patient comfort. As a consequence of the long presence of the expanded device in the urethra, the dilated urethral configuration will tend to remain in such configuration for an extended period of time, even after the device is removed. Up to 12–24 months or more is likely before obstruction of the prostatic urethra will occur again. This is a highly desirable result of this aspect of the invention. As stated above, in the prior means employed for rapidly dilating obstructed portions of the urethra, deformation of the urethral wall will often have a relatively short effect on relieving the obstruction of the prostatic urethra because the latter is caused by the continued pressure exerted by the hypertrophied prostate gland, due to the resilient viscoelastic nature of its tissue, and because of continued hypertrophy.

While the device of this invention can be in the form of a unitary catheter, it is also contemplated that the device can comprise a stent having the aforesaid dilation means and pressure responsive means thereon, which can remain in the dilated urethra for the desired time, and a removable section for inserting the stent, which can include a filling tube for effecting the initial flow of fluid into the stent. Any suitable attachable means can be provided for removing a unitary catheter after deflation of both the dilation means and the pressure responsive means. If the catheter comprises a stent and a removable section, the latter is by its nature removable by the simple act of withdrawing the section after it is detached from the stent. The means for removing the stent from the dilated urethra can be accomplished by any means known in the art, such as the use of clamps or pull strings.

Further objects, features and advantages of the present invention will become apparent from the detailed description of the drawings.

DETAILED DESCRIPTION OF THE DRAWINGS

Figure 1:
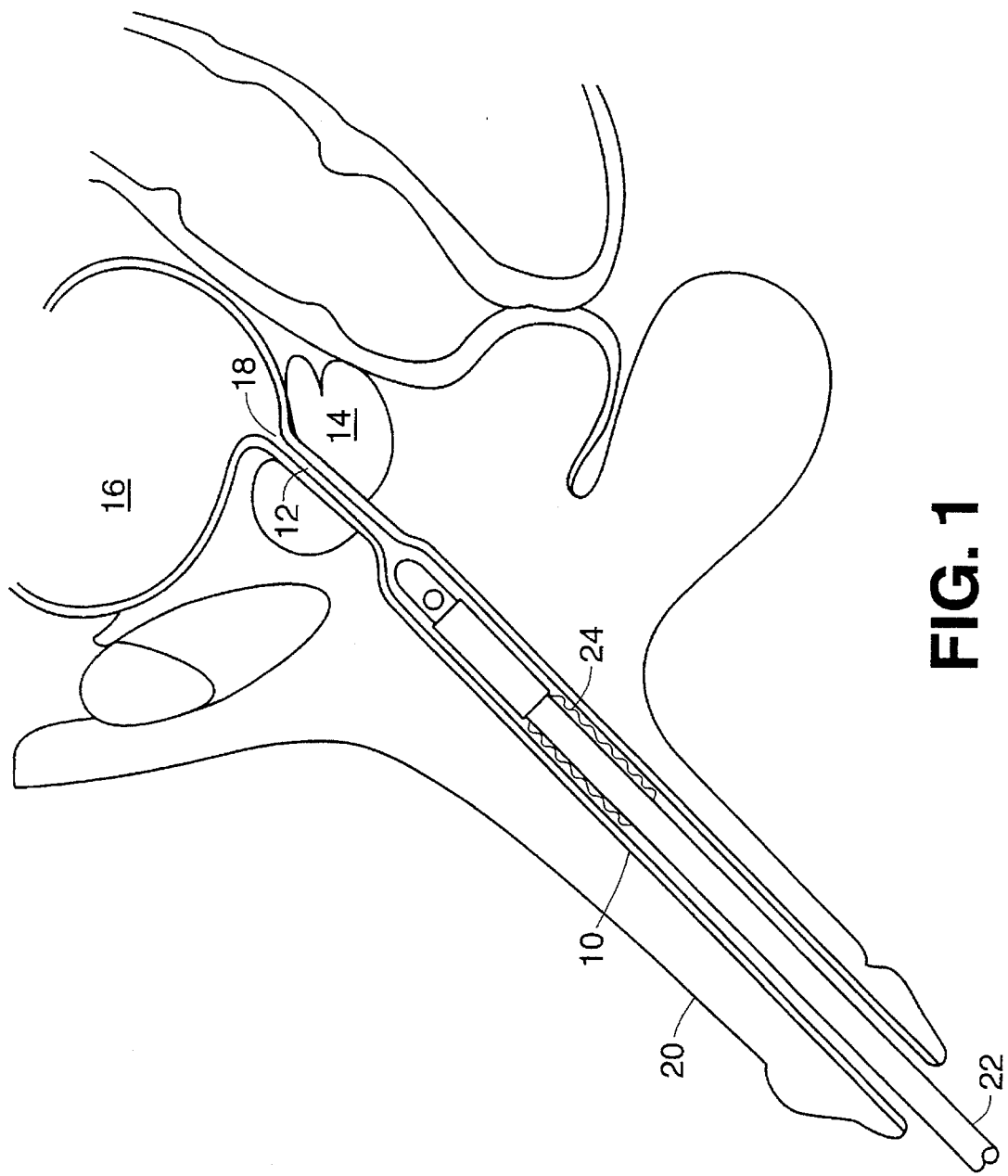
FIG. 1 is a simplified sectional view of the relevant anatomy of a male body, showing an obstructed urethra, an enlarged prostate gland, a bladder, and a schematic unexpanded dilation device of the subject invention, as hereinafter described, which is positioned just before insertion into the obstructed portion of the prostatic urethra.

In the drawings like reference numerals are utilized for like parts throughout the several views. In FIG. 1 there is illustrated, in simplified form, a urethra 10 having an obstructed portion 12 about which is depicted an enlarged hypertrophied prostate gland 14, which inferentially is pressing inwardly on the obstructed portion 12. Also shown is a bladder 16 having a neck 18 depending therefrom, and at the other end of the urethra is a penis 20. A dilation device 22 according to the subject invention, which will be hereinafter described, is shown in position to be inserted into the urethra 10, the device 22 comprising portion 24 having a length at least equal to that of the obstructed portion 12.

Figure 2:
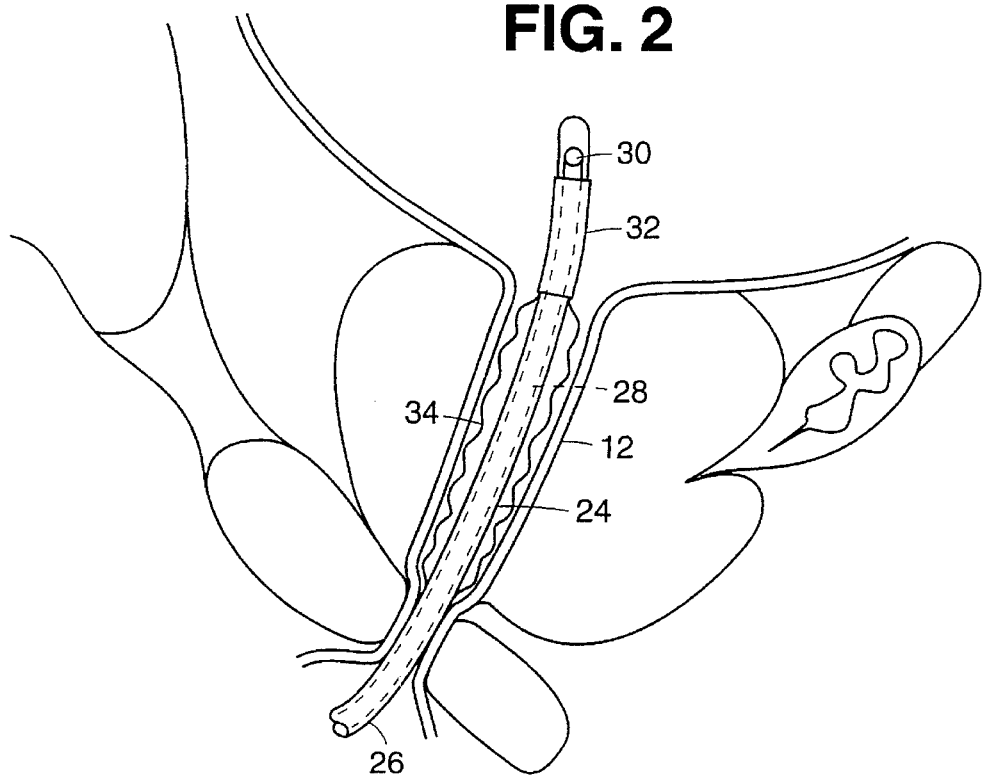
FIG. 2 is a sectional view of a portion of FIG. 1 depicting a portion of the dilation device, in a non-expanded state, implanted within the obstructed portion of the urethra. Pressure responsive means is shown distally disposed inside the bladder.

In FIG. 2 there is shown a simplified sectional view of the portion 24 when placed in the obstructed portion of the urethra. The portion 24 is depicted in an unexpanded mode. Extending through the portion 24 is a draining lumen 28 having a bladder drainage port 30 in the distal portion of the device which communicates with the drainage lumen, for permitting the flow of urine therethrough, i.e., from the bladder through the urethra and out of the penis. Protruding portion 26 can be attached to suitable means for insertion. The lumen 28 acts as a conduit having a diameter sufficient to permit urine to flow therethrough. A pressure responsive inflatable source 32 is shown disposed in the distal portion of the portion 24 which, when secured in the body, would usually be in the area of the bladder neck. Inflatable means 34, which is preferably in the form of a dilation balloon, is disposed along the outer surface of the portion 24 and has a length at least equal to that of the obstructed portion of the urethra.

The portion 24 of the device of the subject invention, wherein the inflatable means is in its unexpanded state, should be of a minimum diameter, including the pressure responsive means and dilation balloon, which would allow the device 22 to be inserted into the penis and then into the obstructed portion of the urethra with a minimum of discomfort. A suitable diameter in this regard should be about 20 to about 26 French. (1 French =⅓ mm). The dilation balloon should be a material capable of expanding outwardly and radically so as to impact upon the obstructed urethra, in order to expand and dilate the obstructed portion 12 of the urethra 10 to a predetermined diameter and (dilated) configuration.

Figure 3:
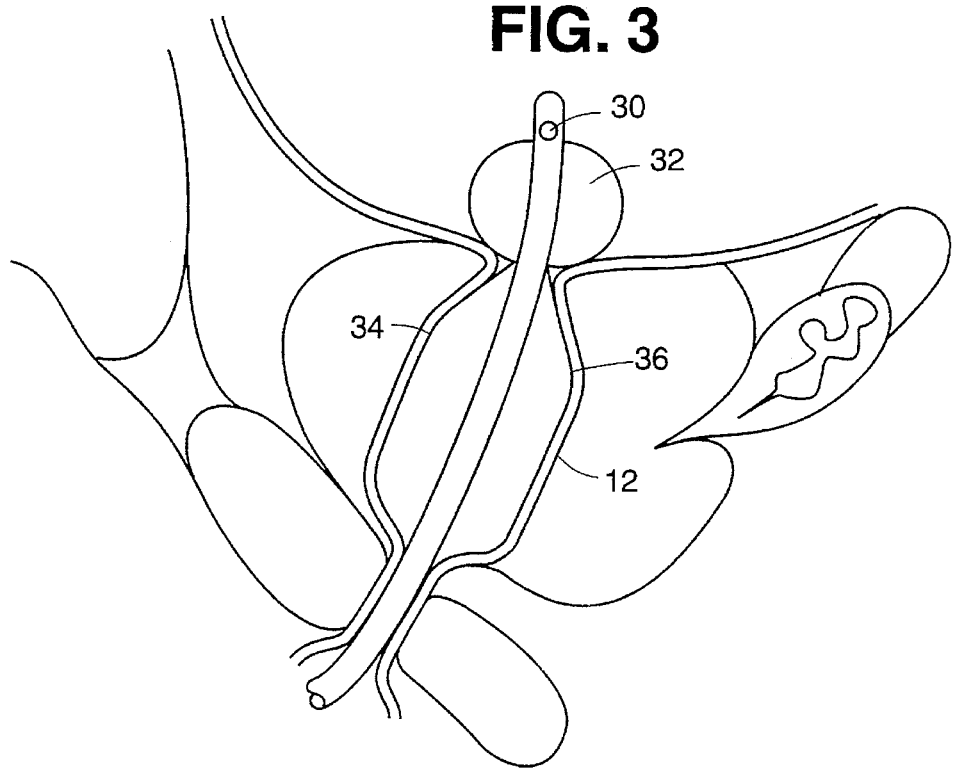
FIG. 3 is a sectional view of the device shown in FIG. 2, in an expanded state, and indicating the concomitant dilation of the prostatic urethra, wherein the pressure responsive means, though partially deflated, is acting as a positioning balloon.

In FIG. 3, the dilation balloon 34 of the dilation device of this invention is shown in an expanded, inflated state with outer surface 36 impacting on the obstructed portion of the urethra. The portion 12 of the urethra, formerly obstructed by the hyperplasia of the prostate gland, is now shown in a dilated configuration. The pressure responsive means or pressure source 32 is initially completely inflated but in the final operable mode of this embodiment wherein the urethra is inflated, the pressure responsive means 32 is only partially inflated; however, it remains sufficiently inflated so that, in this embodiment, it also acts as a positioning balloon, located at the bladder neck.

Figure 4:
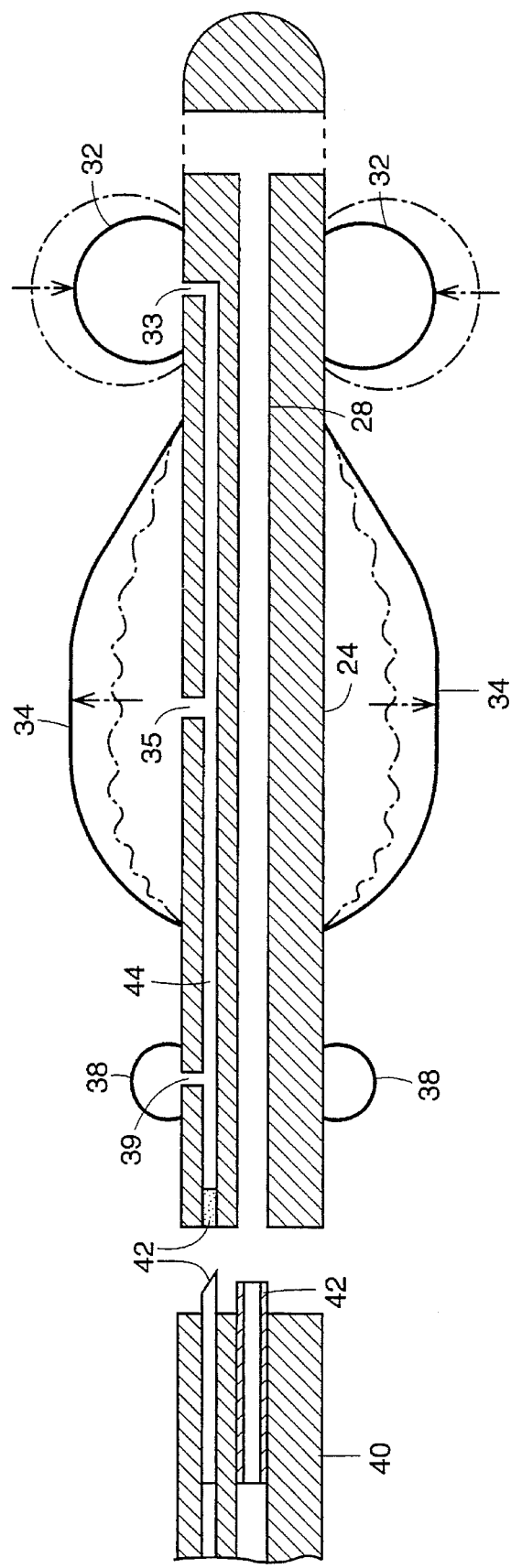
FIG. 4 is a schematic view of a dilation device of this invention, wherein the pressure responsive means and dilation balloon are in fluid communication through a single lumen, the device further comprising a stent portion and a detachable inserter.

In FIG. 4 there is shown a schematic cross-sectional view of another typical device of this invention. As depicted therein, a pressure source 32 is disposed in the distal portion of the device, on the portion 24, which is in the form of a stent, and a dilation envelope 34, which is preferably a balloon such as is normally used in this art, is disposed proximal to but not abutting with the pressure source. Downstream from the dilation balloon, but in this embodiment still a part of the stent, is a location or positioning balloon 38. In this embodiment, the pressure source 32 is adapted to be disposed in the bladder while the positioning balloon 38 is adapted to be disposed in the area of the bulbous urethra. It is also possible in this embodiment for the pressure source to act as an additional positioning means, which will aid in retaining the device within the urethra. The dilation balloon is of a length of at least that of the obstructed portion of the urethra. Also shown in this figure is an attaching inserter member 40 which preferably can be detachable, leaving the stent in the urethra. However, optionally, it is to be understood that the inserter and stent can remain undetached, i.e., the device thereby functioning as a catheter. Means 42, illustratively in the form a needle and septum, for attaching or detaching the catheter, can also be provided.

As stated above, draining lumen 28 extends through the device 22. Location balloon 38, dilation balloon 34 and pressure source 32 are also in fluid communication with each other through lumen 44 which extends through device 22. Port 39 permits the flow of fluid into location balloon 38. Ports 35 and 33 permit the flow of fluid into the dilation balloon 34 and pressure source 32 respectively.

In operation, the passage of fluid from outside the penis through lumen 44 is controlled so that the positioning balloon 38 and the pressure source 32 are fully inflated, but in the context of this invention, the dilation balloon 34 is initially only partially inflated, i.e., to an extent less than that needed to impact with sufficient force to dilate the obstructed portion of the urethra. In a preferred mode of operation, when pressure source 32 contracts due to the pressure differential between that of the pressure source and the pressure exerted on the dilation balloon by the hypertrophied prostate, fluid will flow at a predetermined rate from the pressure source into the dilation balloon so as to slowly and gradually expand the latter to the extent necessary for it to impact with sufficient force to dilate the obstructed portion of the urethra. The rate of this flow can also be determined by the geometry and elastic modulus of the pressure balloon, which will contrast to the resistance of the prostate tissue surrounding the dilation balloon.

Figure 5:
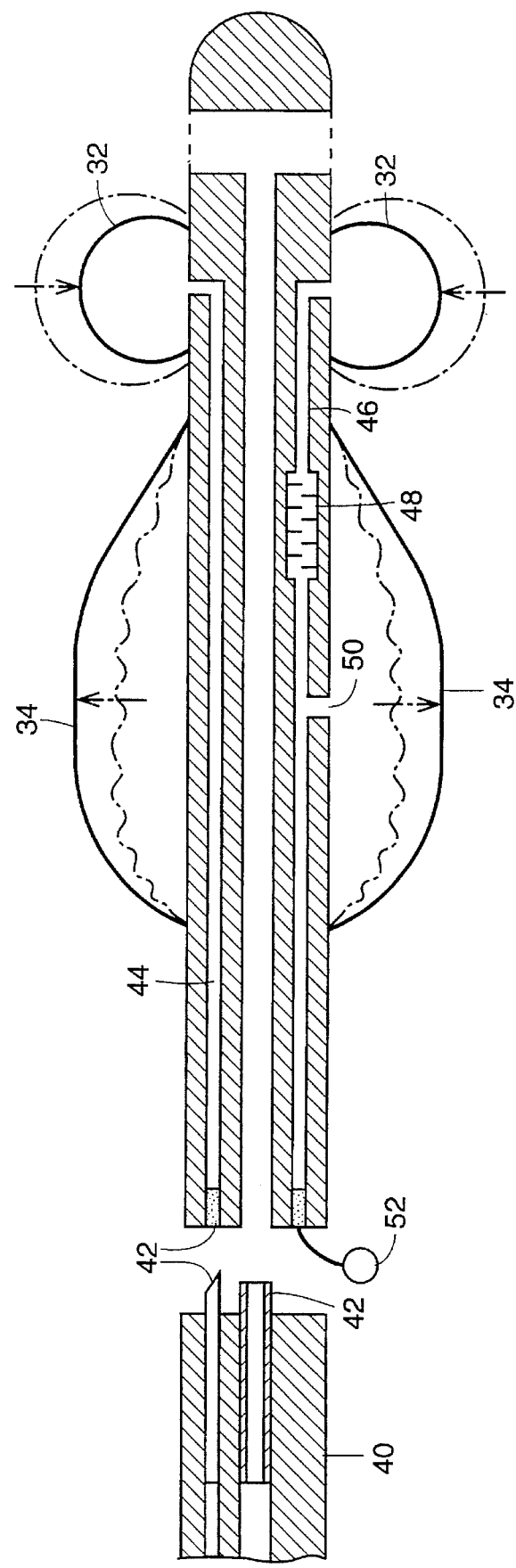
FIG. 5 is a schematic view of a dilation device of this invention wherein the pressure responsive means also serves as a positioning balloon, and a separate lumen provides further fluid communication between the dilation balloon and the pressure responsive/positioning balloon.

In FIG. 5 there is shown an embodiment of this invention in which the pressure responsive balloon 32 also serves as a positioning balloon which would be adapted to be located in the bladder neck. Also shown in this figure is the single lumen 44 which is in fluid communication with the pressure responsive balloon 32 and serves to initially fully inflate the pressure responsive balloon.

However, in this embodiment, separate lumen 46 provides for the passage of fluid from the contracting pressure balloon 32 into the dilation balloon 34, to effect the desired expansion of the latter. Lumen 46, as shown, continues to the end of the stent. Also shown is a fluid resistor 48 (which can be of a type well known in the art) which acts to control the rate of passage of fluid from pressure source 32 to dilation balloon 34 to enable the latter to expand gradually and slowly in accordance with the practice of this invention. The viscosity of the fluid further controls the rate of flow. Port 50 allows fluid to enter the dilation balloon from lumen 46. When deflation of the stent is required in order to remove the stent, a drainage plug 52 can be utilized. A suitable plug is described in U.S. Pat. No. 5,112,306.

It is also to be understood that within the context of this invention that the pressure responsive means can optionally be disposed outside of the body in the form of, for example, a syringe pump or pump bulb. When such means are employed fluid can be transferred into the dilation means by applying suitable pressure in carefully monitored amounts to thereby slowly dilate the dilation means.

As stated above, the diameter of the unexpanded devices of this invention should be on the order of between about 20 and about 26 French. Generally speaking, diameters of less than about 20 French will not permit adequate urination in combination with desired dilation, while the insertion into the meatus of the penis prior to insertion into an obstructed prostatic urethra of an unexpanded device having a diameter of more than about 26 French will usually be too painful for a patient. It thus follows that the diameter of the lumens of the devices of this invention should be fixed within the tolerable limits of the diametral range of the unexpanded device, preferably on or about 20 French.

The gradual, slow dilation of the dilation balloon should occur over a period of at least 30 minutes, and preferably over a much longer period, a dilation which occurs at a rate of about 5 French per 20 hour period being particularly desirable. Thus if a dilated stent of 70 French is desired, and the initial stent diameter was about 20 French, the slow dilation could take as long as 9 or 10 days. A long expansion period may also result in a longer patency for the resulting dilation. In this regard, the device of the subject invention is adapted to remain in the urethra for periods on the order of seven days to 30 days, the latter being a practical upper limit for retention in the urethra for biocompatible reasons, such as possible urinary tract infection, increased inflammation or bacterially based prostatitis.

For reasons which are not completely known, when the device of this invention is removed, the dilated urethra will tend to remain in its dilated configuration for a period on the order of about 12 to about 24 months, or longer, i.e., the patency of the urethral lumen or canal will tend to remain in its dilated state. It is believed that the slow dilation causes pressure necrosis of the tissue with fibrous collagen deposition within the parenchyma of the prostate. The fibrous tissue is not physiologically active thus reducing the ability of the prostate to contract. This scarring of the gland is much like that which occurs in the myocardium after infarction.

It is apparent that other modifications and variations besides those specifically mentioned herein may be made in the devices described herein and depicted in the accompanying drawings without departing from the concept of the present invention.

We claim:

1. A device for slowly dilating an obstructed portion of a urethra which comprises, a urinary catheter for insertion into the urethra, said catheter having a proximal portion and a distal portion;

dilation means capable of expanding radially outwardly, said means being disposed between said proximal and distal portion and having a length of at least that of the obstructed portion of the urethra;

pressure responsive means which is capable of sequentially contracting under pressure;

conduit means which maintains fluid communication between said pressure responsive means and said dilation means, thereby enabling fluid to flow from said pressure responsive means, when the latter is contracing under pressure, into said dilation means to cause the latter to gradually expand radially outawardly until dilation of the obstructed portion of the urethra occurs to a desired diameter and configuration; and positioning means located on said catheter for positioning said device in the urethra, such that said dilation means is located in the obstructed portion of the urethra.

2. A device according to claim 1, wherein the dilation means is capable of expanding radially outwardly at a predetermined rate.

3. A device according to claim 2, wherein the dilation means is capable of expanding at a rate of between about 5 French and about 20 French over a 24-hour period.

4. A device according to claim 3, wherein the pressure responsive means is disposed at or near the distal portion of the catheter and is capable of expanding with the onset of fluid.

5. A device according to claim 4, wherein, with the initial onset of fluid, the pressure responsive means can be fully inflated, but the dilation means is only partially inflated.

6. A device according to claim 4, wherein the pressure responsive means is in the form of an expandable and contractible balloon which can also act as said positioning means when located in the area of the bladder neck of the body.

7. A device according to claim 4, wherein said positioning means is a separate positioning balloon which is adapted to be located in the bulbous urethra of the body.

8. A device according to claim 4, wherein the catheter is comprised of two elements, (1) a stent which incorporates the distal portion of the catheter, the dilation means, the pressure responsive means, the conduit means and the positioning means, and which can remain in the urethra for a time sufficient that the urethra will tend to remain in a dilated configuration even after removal of the stent, and (2) an attaching member which incorporates the proximal portion of the catheter, and which is detachably removable from said stent.

9. A device according to claim 8, wherein the stent is adapted to remain in the urethra for a period of between about 5 days and about 30 days, wherein the dilated urethra will tend to remain in a dilated state for a period of between about 12 and about 24 months.

10. A device according to claim 3, wherein the dilation means has an outer surface capable of expanding radially outwardly for a period of at least about 30 minutes.

11. A device according to claim 6, wherein the dilation means is in the form of an inflatable balloon.

12. A device according to claim 11, wherein the balloon has a defined shape and an intrinsic limit to expansion.

13. A device according to claim 1, wherein fluid communication between the dilation means and the pressure responsive means is a single lumen for effecting both inflation and deflation.

14. A device according to claim 1, which further comprises a separately disposed lumen, which provides further fluid communication between said dilation means and said pressure responsive means; and wherein the pressure responsive means is initially inflated using said conduit means, and during the contracting mode of the pressure responsive means fluid flows from said pressure responsive means to said dilation means through said separately disposed lumen.

15. A device according to claim 14, wherein a fluid resistor is located between the dilation means and pressure responsive means along the path of the separately disposed lumen.

16. A device for slowly dilating an obstructed portion of a urethra which comprises, a urinary catheter for insertion into the prostatic urethra, said catheter having a proximal and a distal portion;

a dilation balloon capable of expanding radially outwardly, said balloon being disposed between said proximal and distal portion and having a length of at least that of the obstructed portion of the urethra;

pressure responsive means in the form of an expandable and contractible balloon which is disposed at or near the distal portion of the catheter;

a lumen which maintains fluid communications between said pressure responsive means and said dilation balloon, thereby enabling fluid to flow from said pressure responsive means, when the latter is contracting under pressure, into the dilation balloon to cause the latter to gradually expand radially outwardly at a rate of between about 5 French and about 20 French over a 24 hour period until dilation of the obstructed portion of the urethra occurs to a desired diameter and configuration;

a fluid resistor located along the path of the lumen; and positioning means located on said catheter for positioning said device in the urethra, such that said dilation means is located in the obstructed portion of the urethra.

17. A device according to claim 16, wherein the pressure responsive means also acts as said positioning means when located in the area of the bladder neck of the body.

18. A device according to claim 16, wherein the catheter is comprised of two elements, (1) a stent which incorporates the distal portion of the catheter, the dilation balloon, the pressure responsive means and the lumen, and which can remain in the urethra for a time sufficient that the urethra will tend to remain in a dilated configuration even after removal of the stent, and (2) an attaching member which incorporates the proximal portion of the catheter and which is detachably removable from said stent.

19. A method of dilating a portion of a urethra obstructed as a consequence of a hypertrophied prostate gland, which comprises the steps of, (1) inserting a device into the obstructed portion of the urethra, said device having a length of at least that of the obstructed portion of the urethra, and said device comprising pressure responsive means capable of expanding and contracting under predetermined conditions, dilation means which is in fluid communication with said pressure responsive means and conduit means which maintains fluid communication between said pressure responsive means and said dilation means;

(2) passing a fluid into the pressure responsive means and the dilation means to effect full inflation of the pressure responsive means and partial inflation of the dilation means; and (3) transferring said fluid from said pressure responsive means into said dilation means to cause the dilation means to expand gradually for a period of at least about 30 minutes, and impact upon the obstructed portion of the urethra with sufficient force to cause said obstructed portion to dilate to a desired diameter and configuration.

20. A method of treating benign prostatic hyperplasia, which comprises, (1) inserting a device into the obstructed portion of a urethra obstructed as a consequence of the prostatic hyperplasia, said device comprising, pressure responsive means capable of expanding and contracting under predetermined conditions, dilation means which is in fluid communication with said pressure responsive means and conduit means which maintains fluid communication between said pressure responsive means and said dilation means;

(2) passing a fluid into the pressure responsive means and the dilation means to effect full inflation of the pressure responsive means and partial inflation of the dilation means;

(3) transferring said fluid from said pressure responsive means into said dilation means to cause the dilation means to expand gradually for a period of at least about 30 minutes, to impact upon the obstructed portion of the urethra with sufficient force to cause said obstructed portion to dilate to a desired diameter and configuration;

(4) leaving the device in the urethra for an extended period of time; and (5) then removing the device from the urethra, the dilated portion of the urethra thereby tending to remain in such dilated configuration.

* * * * *